United States Patent
Nonaka et al.

(10) Patent No.: US 10,229,338 B2
(45) Date of Patent: Mar. 12, 2019

(54) MEDIUM STORING IMAGE PROCESSING PROGRAM, IMAGE PROCESSING METHOD, AND IMAGE PROCESSING DEVICE

(71) Applicant: FUJITSU LIMITED, Kawasaki-shi, Kanagawa (JP)

(72) Inventors: Yusuke Nonaka, Kawasaki (JP); Eigo Segawa, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 37 days.

(21) Appl. No.: 15/633,266

(22) Filed: Jun. 26, 2017

(65) Prior Publication Data
US 2018/0068200 A1 Mar. 8, 2018

(30) Foreign Application Priority Data
Sep. 2, 2016 (JP) ................................ 2016-172039

(51) Int. Cl.
G06K 9/00 (2006.01)
G06K 9/46 (2006.01)
(Continued)

(52) U.S. Cl.
CPC ....... G06K 9/4604 (2013.01); G01N 21/8803 (2013.01); G06T 7/0008 (2013.01);
(Continued)

(58) Field of Classification Search
None
See application file for complete search history.

(56) References Cited

U.S. PATENT DOCUMENTS 5,826,213 A * 10/1998 Kennefick ........... G06F 17/5009
702/35
6,028,948 A * 2/2000 Kil ........................ E01C 23/01
382/108

(Continued)

FOREIGN PATENT DOCUMENTS

JP 2005-114671 A 4/2005
JP 2012-2531 A 1/2012
(Continued)

OTHER PUBLICATIONS

Chiba et al., "Feature-Based Image Mosaicing", IAPR Workshop on Machine Vision Applications, Nov. 17-19, 1998, Makuhari, Chiba, Japan (15 pages).

*Primary Examiner* — Hadi Akhavannik
(74) *Attorney, Agent, or Firm* — Westerman, Hattori, Daniels & Adrian, LLP

(57) ABSTRACT

An image processing method includes: identifying a dark region by binarizing an image captured using an imaging device; generating a line image of the dark region by thinning the dark region; identifying a first multiple pairs of pixels that are included in a pixel group forming the generated line image and are separated from each other by a predetermined threshold or more; calculating a first variance of gradients of lines connecting the respective pairs in the first plurality of pairs; identifying a second plurality of pairs of pixels that are included in the pixel group forming the generated line image and are separated from each other by values smaller than the predetermined threshold; calculating a second variance of gradients of lines connecting the respective pairs in the second plurality of pairs; and evaluating the dark region based on the first variance and the second variance.

11 Claims, 15 Drawing Sheets

152

| LABEL IDENTIFICATION INFORMATION | REGION INFORMATION ITEM | CRACK WIDTH | FIRST VARIANCE | SECOND VARIANCE |
|---|---|---|---|---|
| R101 | LABEL IDENTIFICATION INFORMATION REGION INFORMATION ITEM OF "R101" | OOOO | OOOO | OOOO |
| R102 | LABEL IDENTIFICATION INFORMATION REGION INFORMATION ITEM OF "R102" | OOOO | OOOO | OOOO |
| R103 | LABEL IDENTIFICATION INFORMATION REGION INFORMATION ITEM OF "R103" | OOOO | OOOO | OOOO |
| R104 | LABEL IDENTIFICATION INFORMATION REGION INFORMATION ITEM OF "R104" | OOOO | OOOO | OOOO |
| ... | ... | ... | ... | ... |

(51) Int. Cl.
  *G01N 21/88*   (2006.01)
  *G06T 11/20*   (2006.01)
  *G06T 7/00*    (2017.01)

(52) U.S. Cl.
  CPC .. *G06T 11/203* (2013.01); *G06T 2207/20076* (2013.01); *G06T 2207/30132* (2013.01)

(56) References Cited

U.S. PATENT DOCUMENTS

| | | | | |
|---|---|---|---|---|
| 2013/0044936 A1* | 2/2013 | Wang | G06T 7/0004 | 382/141 |
| 2015/0086083 A1* | 3/2015 | Chaudhry | G06T 7/0004 | 382/108 |
| 2016/0055392 A1* | 2/2016 | Nakano | G06K 9/4633 | 382/173 |

FOREIGN PATENT DOCUMENTS

| | | |
|---|---|---|
| JP | 2012-98045 A | 5/2012 |
| JP | 2013-117409 A | 6/2013 |

\* cited by examiner

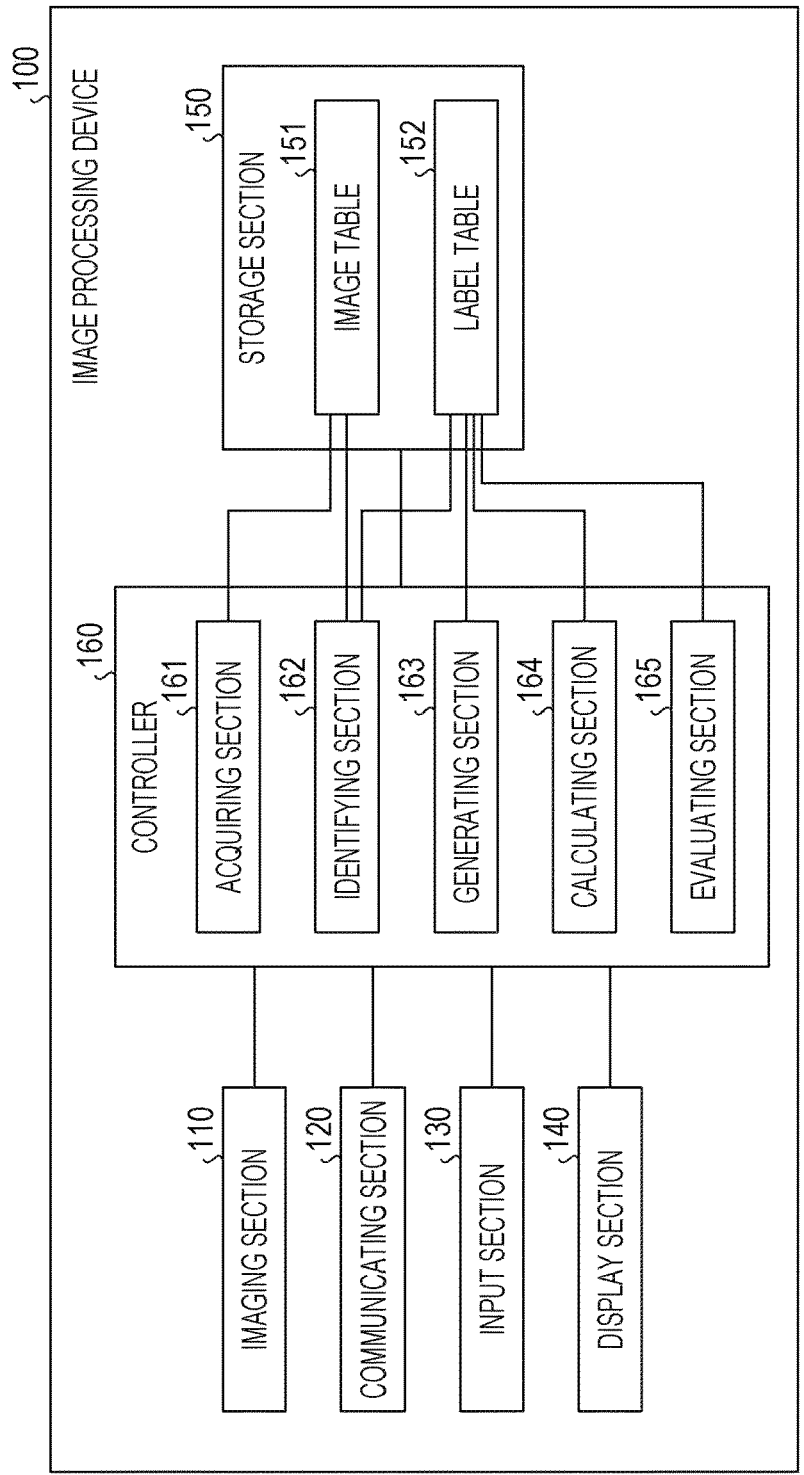

FIG. 2

| LABEL IDENTIFICATION INFORMATION | REGION INFORMATION ITEM | CRACK WIDTH | FIRST VARIANCE | SECOND VARIANCE |
|---|---|---|---|---|
| R101 | LABEL IDENTIFICATION REGION INFORMATION ITEM OF "R101" | ○○○○ | ○○○○ | ○○○○ |
| R102 | LABEL IDENTIFICATION REGION INFORMATION ITEM OF "R102" | ○○○○ | ○○○○ | ○○○○ |
| R103 | LABEL IDENTIFICATION REGION INFORMATION ITEM OF "R103" | ○○○○ | ○○○○ | ○○○○ |
| R104 | LABEL IDENTIFICATION REGION INFORMATION ITEM OF "R104" | ○○○○ | ○○○○ | ○○○○ |
| ⋮ | ⋮ | ⋮ | ⋮ | ⋮ |

FIG. 13

| IMAGING DATE AND TIME | LABEL IDENTIFICATION INFORMATION | REGION INFORMATION ITEM |
|---|---|---|
| 13:00, AUGUST 15, 2016 | R101 | LABEL IDENTIFICATION INFORMATION REGION INFORMATION ITEM OF "R101" |
| | R104 | LABEL IDENTIFICATION INFORMATION REGION INFORMATION ITEM OF "R102" |
| | R115 | LABEL IDENTIFICATION INFORMATION REGION INFORMATION ITEM OF "R103" |
| | R120 | LABEL IDENTIFICATION INFORMATION REGION INFORMATION ITEM OF "R104" |
| ... | ... | ... |
| 13:00, AUGUST 20, 2016 | R205 | LABEL IDENTIFICATION INFORMATION REGION INFORMATION ITEM OF "R101" |
| | R206 | LABEL IDENTIFICATION INFORMATION REGION INFORMATION ITEM OF "R102" |
| | R220 | LABEL IDENTIFICATION INFORMATION REGION INFORMATION ITEM OF "R103" |
| | R250 | LABEL IDENTIFICATION INFORMATION REGION INFORMATION ITEM OF "R104" |
| ... | ... | ... |

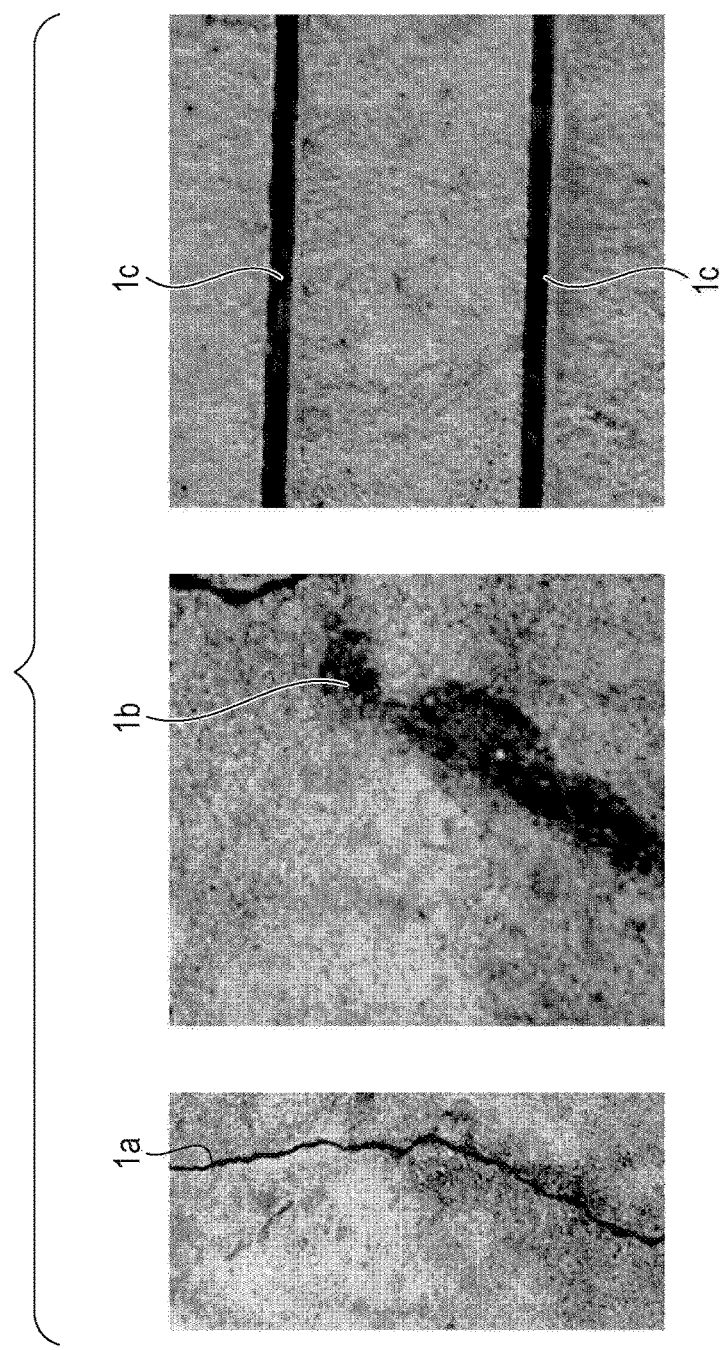

MEDIUM STORING IMAGE PROCESSING PROGRAM, IMAGE PROCESSING METHOD, AND IMAGE PROCESSING DEVICE

CROSS-REFERENCE TO RELATED APPLICATION

This application is based upon and claims the benefit of priority of the prior Japanese Patent Application No. 2016-172039, filed on Sep. 2, 2016, the entire contents of which are incorporated herein by reference.

FIELD

The embodiments discussed herein are related to a program medium, a method and a device for image processing.

BACKGROUND

Workers inspect whether or not a crack exists on wall surfaces of structures such as bridges and tunnels. In order to reduce workers' inspection workload, there is a conventional technique for remotely capturing images of the wall surfaces of the structures and detecting a crack from the captured images. As examples of the conventional technique for detecting a crack from images, conventional techniques 1 and 2 are described below.

The conventional technique 1 (Japanese Laid-open Patent Publication No. 2012-98045) is to treat, as crack candidates, polygonal lines obtained by combining long straight lines and determine whether each of the crack candidates is a crack based on line segment likelihoods of local segments of the polygonal lines and polygonal line likelihoods obtained when the local segments are combined. In the conventional technique 1, similarities between line segments of the local segments and an approximate straight line are used as the line segment likelihoods, and line segment likelihoods of the line segments forming the polygonal lines are used as the polygonal line likelihoods.

The conventional technique 2 (Japanese Laid-open Patent Publication No. 2012-002531) is to determine that a crack candidate is not a crack if the crack candidate is a straight line extending in a horizontal or vertical direction. Other related-art techniques are Japanese Laid-open Patent Publications Nos. 2005-114671 and 2013-117409.

The aforementioned conventional techniques, however, have a problem in which the accuracy of determining whether or not a target object is a crack is low.

For example, a certain wall surface has a characteristic that is not a crack and is dirt, a groove of a structure, or the like and is similar to a crack. FIG. 16 is a diagram illustrating an example of a crack, dirt, and a groove of a structure. As illustrated in FIG. 16, a crack 1a, dirt 1b, and a groove 1c of a structure have similar characteristics. It is, therefore, difficult to accurately identify the crack.

In the conventional technique 1, it may be determined that non-linear dirt is not a crack, but it may be erroneously determined that a linear object such as a groove of a structure is a crack. In addition, in the conventional technique 1, if a target object is a crack and line segments forming a polygonal line are short, similarities between line segments of local segments and an approximate straight line are low and the detection of the crack may fail.

In the conventional technique 2, if a groove of a structure is not set to a line extending in a horizontal or vertical direction for imaging of a wall, the groove of the structure may be erroneously detected as a crack.

According to an aspect, an object of the present disclosure is to provide an image processing program, an image processing method, and an image processing device that may improve the accuracy of determining whether or not a target object is a crack.

SUMMARY

According to an aspect of the invention, an image processing method to be executed by a computer, including: identifying a dark region by binarizing an image captured using an imaging device; generating a line image corresponding to the dark region by thinning the identified dark region; identifying a first plurality of pairs of pixels that are included in a pixel group forming the generated line image and are separated from each other by a predetermined threshold or more; calculating a first variance of gradients of lines connecting the pixels forming the respective pairs in the first plurality of pairs of pixels; identifying a second plurality of pairs of pixels that are included in the pixel group forming the generated line image and are separated from each other by values smaller than the predetermined threshold; calculating a second variance of gradients of lines connecting the pixels forming the respective pairs in the second plurality of pairs of pixels; and evaluating the dark region based on the first variance and the second variance.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 1 is a block diagram illustrating a functional configuration of an image processing device according to a first embodiment;

FIG. 2 is a diagram illustrating an example of a data structure of a label table according to the first embodiment;

FIG. 13 is a diagram illustrating an example of a data structure of a history record table;

FIG. 16 is a diagram illustrating an example of a crack, dirt, and a groove of a structure.

DESCRIPTION OF EMBODIMENTS

Figure 3:
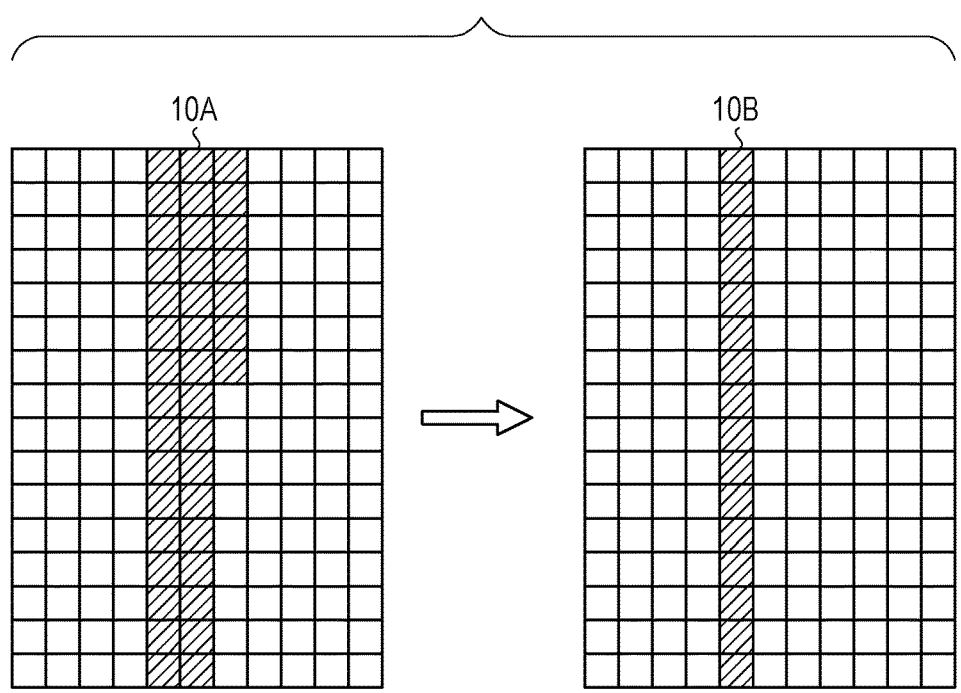
FIG. 3 is a diagram describing an example of a thinning process by a generating section.

Hereinafter, embodiments of an image processing program disclosed herein, an image processing method disclosed herein, and an image processing device disclosed herein are described in detail with reference to the accompanying drawings. The techniques disclosed herein are not limited by the embodiments.

First Embodiment

FIG. 1 is a block diagram illustrating a functional configuration of an image processing device according to a first embodiment. As illustrated in FIG. 1, the image processing device 100 includes an imaging section 110, a communicating section 120, an input section 130, a display section 140, a storage section 150, and a controller 160.

The imaging section 110 is a camera that captures an image included in an imaging range of the imaging section 110. For example, the imaging section 110 captures an image of an object from which a crack may be detected. The imaging section 110 may capture images at predetermined time intervals. The imaging section 110 may capture an image when receiving a capture command. The imaging section 110 may be installed in an unmanned aircraft such as a drone and capture an image.

The imaging section 110 outputs information of a captured image to the controller 160. The information of the image captured by the imaging section 110 is referred to as image data. The imaging section 110 may be connected to the image processing device 100 via a network and transmit the image data to the image processing device 100, but a description thereof with reference to FIG. 1 is omitted.

The communicating section 120 is a processing section that communicates with an external device used by an administrator or the like via a network. The communicating section 120 corresponds to a communicating device such as a network interface card (NIC).

The input section 130 is an input device that causes various types of information to be input to the controller 160. For example, the input section 130 corresponds to a keyboard, a mouse, a touch panel, or the like.

The display section 140 is a display device that displays the results of processes by the controller 160. For example, the display section 140 corresponds to a liquid crystal display, a touch panel, or the like.

The storage section 150 includes an image table 151 and a label table 152. The storage section 150 corresponds to a semiconductor memory element such as a random access memory (RAM), a read only memory (ROM), or a flash memory or a storage device such as a hard disk drive (HDD).

The image table 151 is a table for storing image data captured by the imaging section 110.

The label table 152 is a table for storing information on crack labels. The crack labels and a data structure of the label table 152 are described later.

The controller 160 includes an acquiring section 161, an identifying section 162, a generating section 163, a calculating section 164 and an evaluating section 165. The controller 160 may be achieved by a central processing unit (CPU) or a micro processing unit (MPU). Alternatively, the controller 160 may be achieved by hard-wired logic such as an application specific integrated circuit (ASIC) or a field programmable gate array (FPGA).

The acquiring section 161 is a processing section that acquires image data from the imaging section 110. Every time the acquiring section 161 acquires image data from the imaging section 110, the acquiring section 161 registers the acquired image data in the image table 151.

The identifying section 162 is a processing section that acquires image data from the image table 151, binarizes the image data, and identifies a dark region. For example, the identifying section 162 uses a technique such as discriminant analysis or the Niblack method to binarize the image data and generate a binary image. The identifying section 162 labels, as a same portion, the portion in which the dark region is continuous in the binary image. The labeled portion in which the dark region is continuous is referred to as a crack label. The identifying section 162 registers information of the crack label in the label table 152. If the length of the portion in which the dark region is continuous is equal to or larger than a predetermined value, the portion may be divided into multiple portions having appropriate lengths smaller than the predetermined value, and the multiple portions may be processed.

FIG. 2 is a diagram illustrating an example of a data structure of the label table according to the first embodiment. As illustrated in FIG. 2, in the label table 152, label identification information, region information items, crack widths, first variances, and second variances are associated with each other. The label identification information uniquely identifies crack labels. The region information items include positional coordinates of pixels included in the crack labels. The crack widths correspond to the widths of the crack labels and are calculated by the generating section 163 described later. The first variances and the second variances are calculated by the calculating section 164 described later.

The generating section 163 is a processing section that acquires information of the crack labels from the label table 152 and generates thinned crack labels. For example, the generating section 163 thins the crack labels by changing the numbers of pixels of the crack labels in the directions of short sides among short and long sides of the crack labels to 1.

FIG. 3 is a diagram illustrating an example of a thinning process to be executed by the generating section. As illustrated in FIG. 3, the generating section 163 thins a crack label 10A to generate a crack label 10B by changing the number of pixels in the direction of a short side of the crack label 10A to 1. In addition, the generating section 163 calculates a crack width by dividing the number of pixels of the crack label 10A before the thinning by the number of pixels of the crack label 10B after the thinning. The generating section 163 updates the region information items of the label table 152 based on the crack label 10B after the thinning and registers information of the corresponding crack width. The generating section 163 repeatedly executes the aforementioned thinning process on crack labels before the thinning. In the following description, a crack label after the thinning is merely referred to as crack label.

The calculating section 164 identifies first multiple pairs of pixels that are included in a pixel group forming a crack label and are separated from each other by distances equal to or greater than a predetermined threshold, and calculates a first variance of gradients connecting the pixels in the respective identified first multiple pairs of pixels. In addition, the calculating section 164 identifies second multiple pairs of pixels that are included in the pixel group forming the crack label and are separated from each other by distances smaller than the predetermined threshold, and calculates a second variance of gradients connecting the pixels in the respective identified second multiple pairs of pixels.

Figure 4:
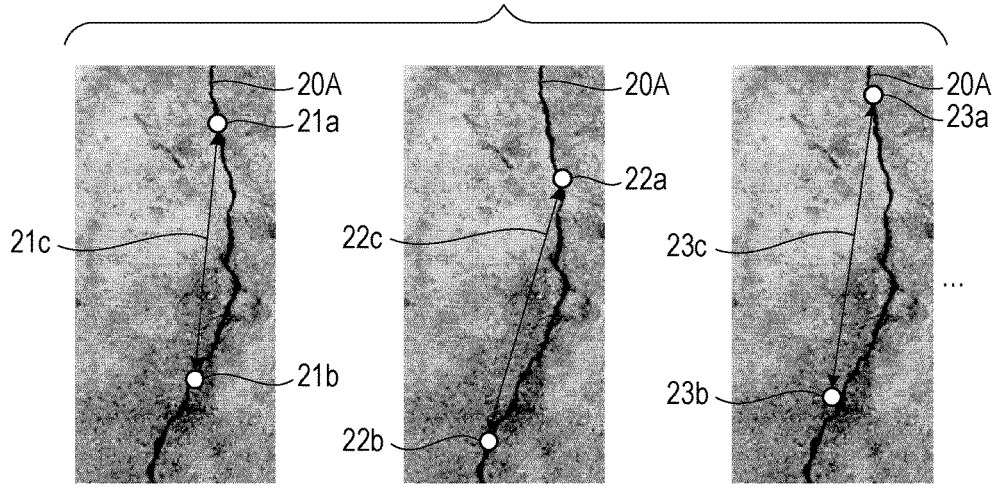
FIG. 4 is a first diagram describing a process by a calculating section according to the first embodiment.
Figure 5:
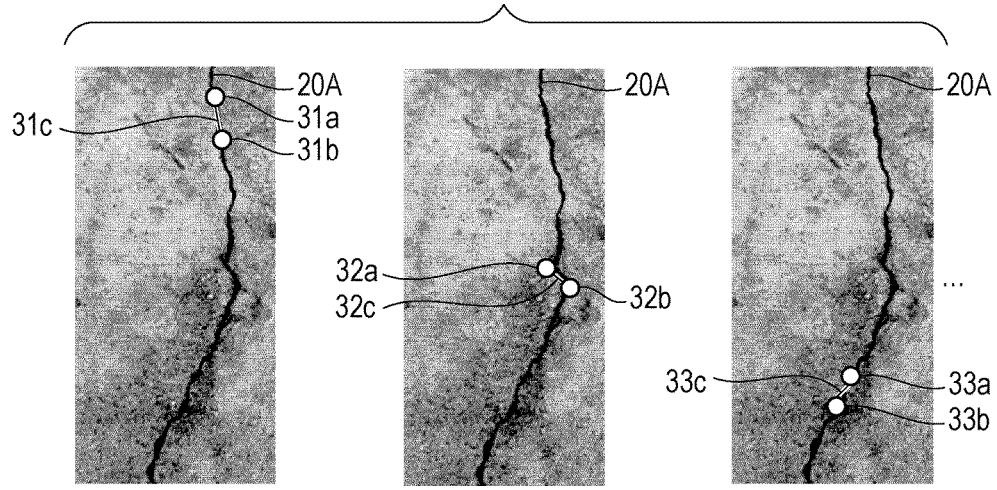
FIG. 5 is a second diagram describing the process by the calculation section according to the first embodiment.

FIGS. 4 and 5 are diagrams describing a process to be executed by the calculating section 164 according to the first embodiment. FIG. 4 is described below. As an example, a crack label 20A is selected. The calculating section 164 identifies the first multiple pairs of pixels that are included in a pixel group forming the crack label 20A and are separated from each other by the predetermined threshold or more. The pairs of pixels may be all possible pairs of pixels or may be randomly selected so that a statistically effective result is obtained from the selected pixel pairs. In the example illustrated in FIG. 4, the calculating section 164 identifies a pair of pixels 21a and 21b, a pair of pixels 22a and 22b, and a pair of pixels 23a and 23b. A line that connects the pixels 21a and 21b to each other is indicated by 21c. A line that connects the pixels 22a and 22b to each other is indicated by 22c. A line that connects the pixels 23a and 23b to each other is indicated by 23c.

The calculating section 164 calculates a first variance by calculating the variance of gradients of the lines 21c, 22c, and 23c.

FIG. 5 is described below. As an example, the crack label 20A is selected. The calculating section 164 identifies the second multiple pairs of pixels that are included in a pixel group forming the crack label 20A and are separated from each other by values smaller than the predetermined threshold. In the example illustrated in FIG. 5, the calculating section 164 identifies a pair of pixels 31a and 31b, a pair of pixels 32a and 32b, and a pair of pixels 33a and 33b. A line that connects the pixels 31a and 31b to each other is indicated by 31c. A line that connects the pixels 32a and 32b to each other is indicated by 32c. A line that connects the pixels 33a and 33b to each other is indicated by 33c.

The calculating section 164 calculates a second variance by calculating the variance of gradients of the lines 31c, 32c, and 33c.

The calculating section 164 registers information of the first and second variances corresponding to the crack label 20A in the label table 152. The calculating section 164 repeatedly executes the process of calculating first and second variances for other crack labels and registers the results of the calculation in the label table 152.

The evaluating section 165 is a processing section that evaluates the crack labels of the label table 152 and identifies a crack label corresponding to a crack. Specifically, the evaluating section 165 determines that a crack label of which a first variance is smaller than a first standard variance and of which a second variance is larger than a second standard variance is a crack.

The evaluating section 165 adjusts the standard variances based on the crack width of a crack label to be evaluated. For example, the evaluating section 165 compares the crack width of the crack label to be evaluated with a table (not illustrated) in which standard variances are associated with crack widths, and identifies standard variances to be used for the evaluation. In the table, as a crack width becomes larger, standard variances associated with the crack width become larger.

The evaluating section 165 repeatedly executes the process of evaluating a crack label and identifies a crack label as a crack. The evaluating section 165 generates image information indicating the position of the crack label identified as the crack and causes the display section 140 to display the generated image information.

Figure 6:
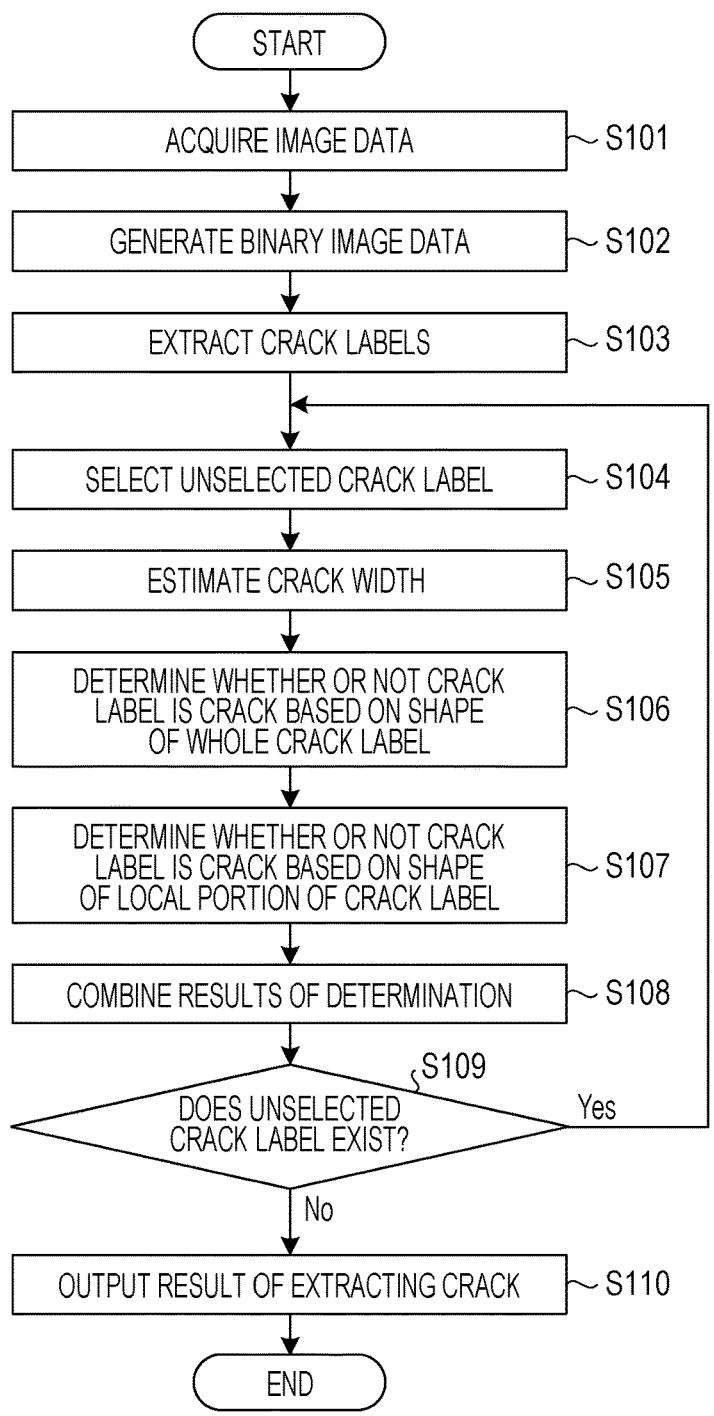
FIG. 6 is a flowchart of a process procedure of the image processing device according to the first embodiment.

Next, a process procedure of the image processing device 100 according to the first embodiment is described. FIG. 6 is a flowchart of the process procedure of the image processing device according to the first embodiment. As illustrated in FIG. 6, the acquiring section 161 of the image processing device 100 acquires image data (in step S101). The identifying section 162 of the image processing device 100 generates binary image data from the acquired image data (in step S102). The identifying section 162 extracts crack labels (in step S103).

The calculating section 164 of the image processing device 100 selects an unselected crack label (in step S104) and estimates the crack width of the selected crack label (in step S105). The evaluating section 165 of the image processing device 100 determines whether or not the crack label is a crack based on the shape of the whole crack label (in step S106). In step S106, the evaluating section 165 determines whether or not a first variance of the selected crack label is smaller than the first standard variance.

The evaluating section 165 determines whether or not the crack label is a crack based on the shapes of local portions of the crack label (in step S107). In step S107, the evaluating section 165 determines whether or not a second variance of the selected crack label is larger than the second standard variance.

The evaluating section 165 combines the results of the determination (in step S108). In step S108, if the first variance is smaller than the first standard variance and the second variance is larger than the second standard variance, the evaluating section 165 determines that the selected crack label is a crack.

The evaluating section 165 determines whether or not an unselected crack label exists (in step S108). If the unselected crack label exists (Yes in step S109), the evaluating section 165 causes the process to return to step S104.

On the other hand, if the unselected crack label does not exist (No in step S109), the evaluating section 165 outputs the result of extracting a crack (in step S110).

Next, effects of the image processing device 100 according to the first embodiment are described. If a first variance of a selected crack label is smaller than the first standard variance and a second variance of the selected crack label is larger than the second standard variance, the image processing device 100 determines that the selected crack label is a crack. Thus, the accuracy of determining whether or not a target object is a crack may be improved.

When a whole crack is seen, the crack may extend in a single direction. However, when local portions of the crack are seen, the local portions may extend in various directions. On the other hand, dirt and a groove of a structure do not have the aforementioned characteristics of the crack. Thus, the image processing device 100 uses a first variance for a whole crack label and a second variance for local portions of the crack label and may accurately identify a crack.

Second Embodiment

Figure 7:
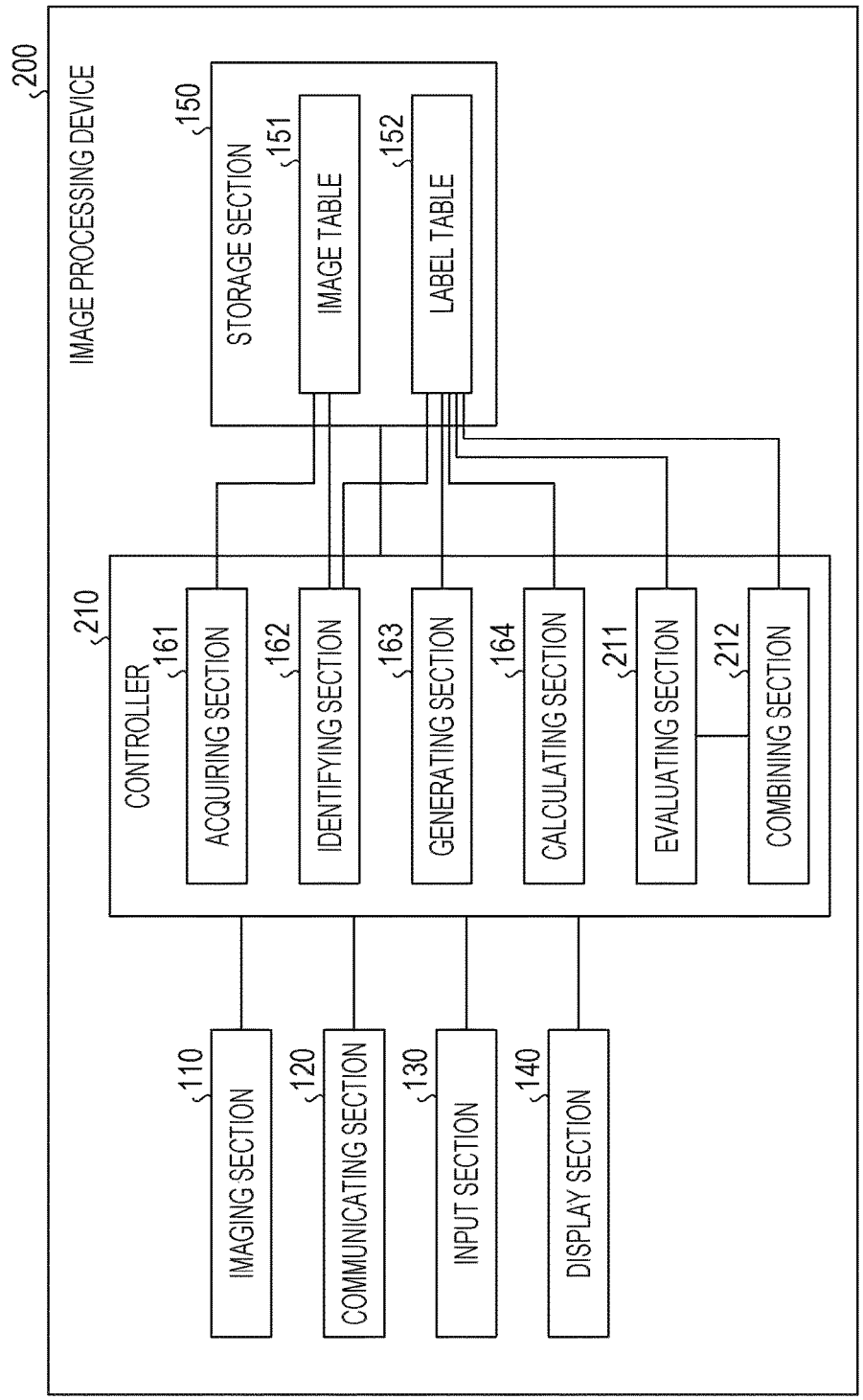
FIG. 7 is a block diagram illustrating a functional configuration of an image processing device according to a second embodiment.

FIG. 7 is a block diagram illustrating a functional configuration of an image processing device according to a second embodiment. As illustrated in FIG. 7, the image processing device 200 includes an imaging section 110, a communicating section 120, an input section 130, a display section 140, and a storage section 150, and a controller 210. A description of the imaging section 110, the communicating section 120, the input section 130, the display section 140, and the storage section 150 is the same as or similar to the description of the imaging section 110, the communicating section 120, the input section 130, the display section 140, and the storage section 150 with reference to FIG. 1.

The controller 210 includes an acquiring section 161, an identifying section 162, a generating section 163, a calculating section 164, an evaluating section 211, and a combining section 212. The controller 210 may be achieved by a CPU, an MPU, or the like. Alternatively, the controller 210 may be achieved by hard-wired logic such as an ASIC or an FPGA. A description of the acquiring section 161, the identifying section 162, the generating section 163, and the calculating section 164 is the same as or similar to the description of the acquiring section 161, the identifying section 162, the generating section 163, and the calculating section 164 with reference to FIG. 1.

The evaluating section 211 is a processing section that evaluates crack labels of the label table 152 and identifies a crack label corresponding to a crack. A process of evaluating crack labels by the evaluating section 211 is the same as or similar to the process to be executed by the evaluating section 165 described in the first embodiment. The evaluating section 211 evaluates the crack labels and outputs label identification information of a crack label that does not correspond to a crack.

The evaluating section 211 re-evaluates crack labels obtained by combining crack labels by the combining section 212 and identifies a crack label corresponding to a crack.

The combining section 212 is a processing section that selects two crack labels from among multiple crack labels evaluated by the evaluating section 211 as crack labels that do not correspond to cracks. If the selected crack labels satisfy a predetermined requirement, the combining section 212 combines the selected crack labels.

Figure 8:
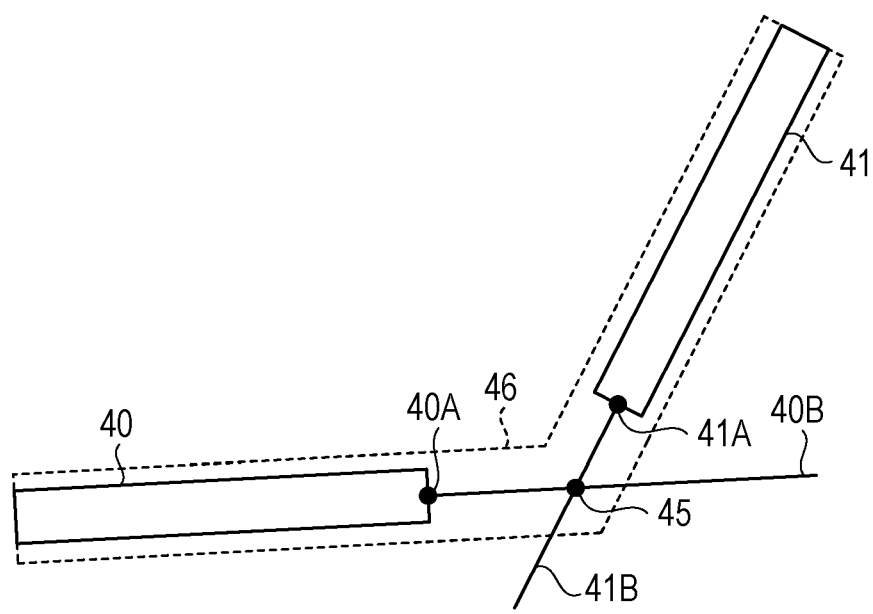
FIG. 8 is a diagram describing a process to be executed by a combining section.

FIG. 8 is a diagram describing a process to be executed by the combining section. FIG. 8 describes a case where the combining section 212 selects crack labels 40 and 41. The combining section 212 selects a combination of a pixel included in the crack label 40 and closest to a pixel included in the crack label 41 among pixels included in the crack labels 41, and the pixel included in the crack label 41 and closest to the pixel included in the crack label 40 among pixels included in the crack label 40. For example, the combining section 212 selects a pixel 40A included in the crack label 40 and a pixel 41A included in the crack label 41. If the distance between the pixels 40A and 41A is shorter than a threshold, the combining section 212 executes the following process.

The combining section 212 calculates a straight line 40B extending from the pixel 40A in a longitudinal direction (from one of both edges of the label 40 to the other edge of the label 40) of the label 40. The combining section 212 calculates a straight line 41B extending from the pixel 40B in a longitudinal direction (from one of both edges of the label 41 to the other edge of the label 41) of the label 41. The combining section 212 calculates an intersection 45 at which the straight lines 40B and 41B intersect with each other.

The combining section 212 combines, into a single crack label 46, the crack label 40, pixels located on a line segment extending from the pixel 40A to the intersection 45, pixels located on a line segment extending from the intersection 45 to the pixel 41A, and the crack label 41. The combining section 212 registers information of the combined crack label 46 in the label table 152.

If the distance between the pixels 40A and 41A is equal to or longer than the threshold, the combining section 212 skips the aforementioned combination process and selects another pair of crack labels. Then, the combining section 212 selects a combination of a pixel included in one of the selected crack labels and closest to a pixel included in the other selected crack label among pixels included in the other selected crack label and the pixel included in the other selected crack label and closest to the pixel included in the one of the selected crack labels among pixels included in the one of the selected crack labels and executes the process of determining whether or not the distance between the pixels are equal to or longer than the threshold.

The combining section 212 repeatedly executes the aforementioned process on multiple pairs of crack labels evaluated as crack labels that do not correspond to cracks.

Figure 9:
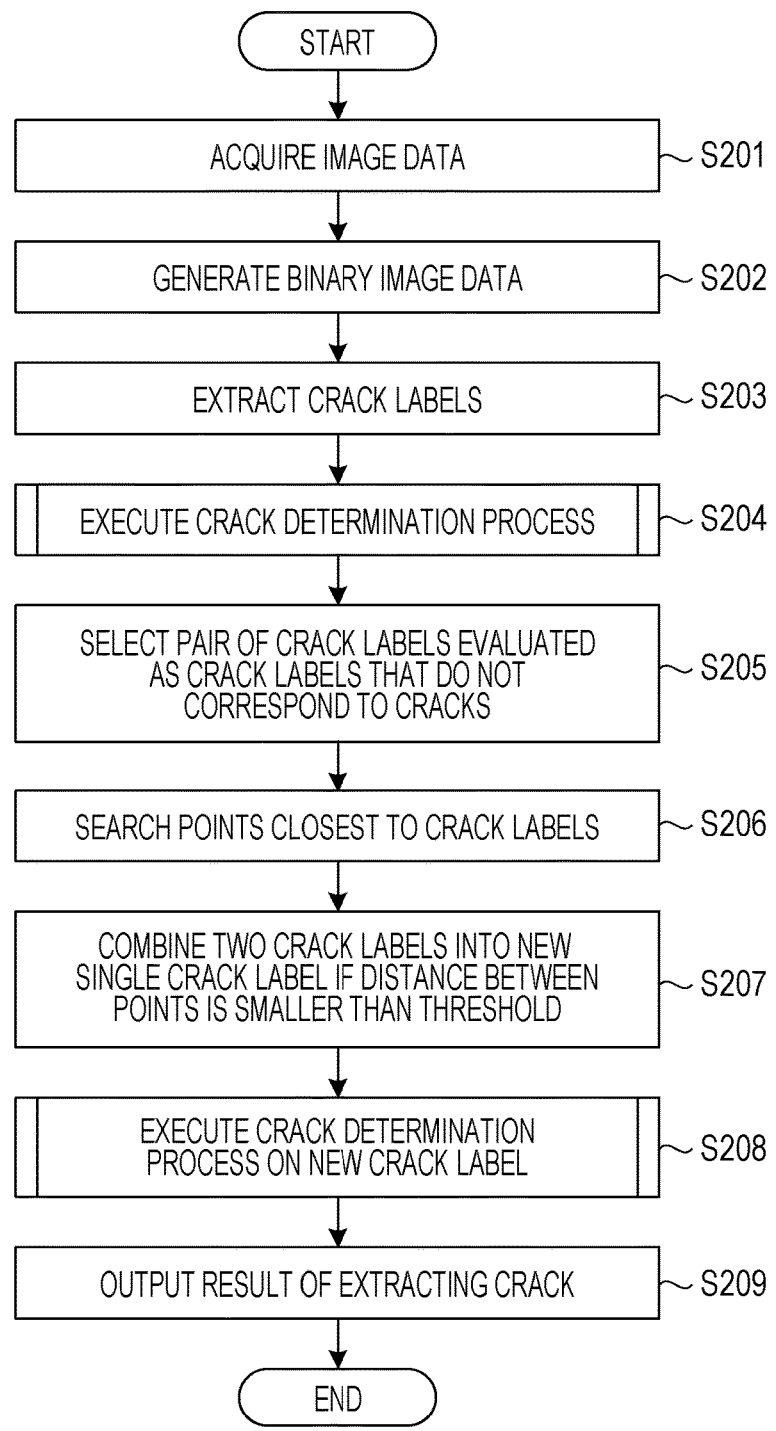
FIG. 9 is a flowchart of a process procedure of the image processing device according to the second embodiment.

Next, a process procedure of the image processing device 200 according to the second embodiment is described. FIG. 9 is a flowchart of the process procedure of the image processing device according to the second embodiment. As illustrated in FIG. 9, the acquiring section 161 of the image processing device 200 acquires image data (in step S201). The identifying section 162 of the image processing device 200 generates binary image data from the acquired image data (in step S202). The identifying section 162 extracts crack labels (in step S203).

The evaluating section 211 executes a crack determination process (in step S204). The crack determination process of step S204 corresponds to the processes of steps S104 to S109 illustrated in FIG. 6.

The combining section 212 of the image processing device 200 selects a pair of crack labels evaluated as crack labels that do not correspond to cracks (in step S205). The combining section 212 searches a point (pixel) included in one of the selected crack labels and closest to a point (pixel) included in the other selected crack label among points (pixels) included in the other selected crack label and the point (pixel) included in the other selected crack label and closest to the point (pixel) included in the one of the selected crack labels among points (pixels) included in the one of the selected crack labels (in step S206).

If the distance between the points is smaller than the threshold, the combining section 212 combines the two crack labels to generate a new single crack label (in step S207). The evaluating section 211 executes the crack determination process on the new crack label (in step S208). The crack determination process of step S208 corresponds to the processes of steps S104 to S109 illustrated in FIG. 6. The crack label to be processed is the new crack label combined by the combining section 212. The evaluating section 211 outputs the result of extracting a crack (in step S209).

Next, effects of the image processing device 200 according to the second embodiment are described. If crack labels determined as crack labels that do not correspond to cracks satisfy the predetermined requirement, the image processing device 200 combines the crack labels into a single crack label and re-evaluates the combined crack label. If a disconnected crack is a linear crack, the disconnected crack is evaluated as an object that is not a crack, but may be detected by the aforementioned combination process.

In addition, the image processing device 200 according to the second embodiment selects a pair of a pixel that is among pixels included in one of crack labels evaluated as non-cracks and is closest to a pixel included in the other crack label evaluated as a non-crack among pixels included in the other crack label and the pixel that is among pixels included in the other crack label evaluated as the non-crack and is closest to the pixel included in the one of the crack labels evaluated as the non-cracks among pixels included in the one of the crack labels. If the distance between the selected pixels is shorter than the threshold, the image processing device 200 executes the process of combining the crack labels. Thus, an erroneous combination of crack labels may be suppressed. In addition, since a pair of crack labels that are not combined is quickly removed from crack labels to be processed, the processing load may be reduced.

Third Embodiment

Figure 10:
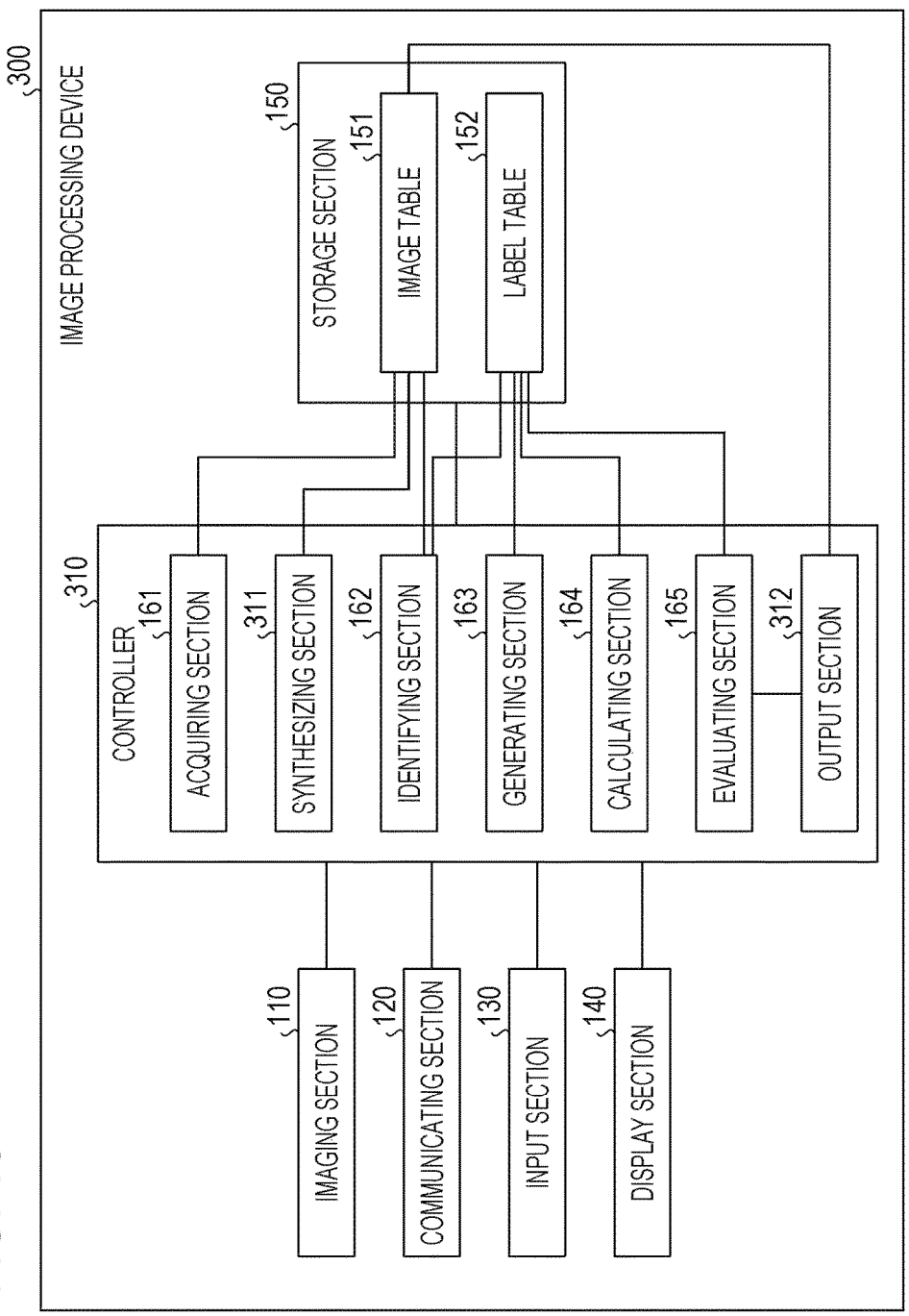
FIG. 10 is a block diagram illustrating a functional configuration of an image processing device according to a third embodiment.

FIG. 10 is a block diagram illustrating a functional configuration of an image processing device according to a third embodiment. As illustrated in FIG. 10, the image processing device 300 includes an imaging section 110, a communicating section 120, an input section 130, a display section 140, a storage section 150, and a controller 310. A description of the imaging section 110, the communicating section 120, the input section 130, the display section 140, and the storage section 150 is the same as or similar to the description of the imaging section 110, the communicating section 120, the input section 130, the display section 140, and the storage section 150 with reference to FIG. 1.

The controller 310 includes an acquiring section 161, an identifying section 162, a generating section 163, a calculating section 164, an evaluating section 165, a synthesizing section 311, and an output section 312. The controller 310 may be achieved by a CPU, an MPU, or the like. Alternatively, the controller 310 may be achieved by hard-wired logic such as an ASIC or an FPGA. A description of the acquiring section 161, the identifying section 162, the generating section 163, the calculating section 164, and the evaluating section 165 is the same as or similar to the description of the acquiring section 161, the identifying section 162, the generating section 163, the calculating section 164, and the evaluating section 165 with reference to FIG. 1.

The synthesizing section 311 is a processing section that synthesizes image data stored in the image table 151 to generate synthesized image data of a single image indicating a whole target object. For example, the synthesizing section 311 may synthesize the image data based on a document ("Feature-Based Image Mosaicing", Naoki Chiba, Hiroshi Kano, Michihiko Minoh, and Masashi Yasuda, The transactions of the Institute of Electronics, Information and Communication Engineers, D-II, Vol. J82-D-II, No. 10, pp. 1581-1589). The synthesizing section 311 registers the synthesized image data in the image table 151.

Processes to be executed by the identifying section 162, the generating section 163, the calculating section 164, and the evaluating section 165 are basically the same as or similar to the processes to be executed by the identifying section 162, the generating section 163, the calculating section 164, and the evaluating section 165 that are described with reference to FIG. 1. The identifying section 162, the generating section 163, the calculating section 164, and the evaluating section 165 may evaluate a crack based on the synthesized image data of multiple images or may evaluate the crack using the synthesized image data as image data of a single image.

The output section 312 acquires the results of the evaluation by the evaluating section 165 and identifies crack labels determined as cracks. The output section 312 acquires synthesized image data from the image table 151 and generates an image that is to be output and in which marks are located at crack labels determined as cracks on the synthesized image data. Then, the output section 312 outputs the generated image to the display section 140 and causes the display section 140 to display the output image. For example, the output section 312 visualizes the cracks on the synthesized image data by causing the display section 140 to display pixels corresponding to the crack labels in a predetermined color.

Figure 11:
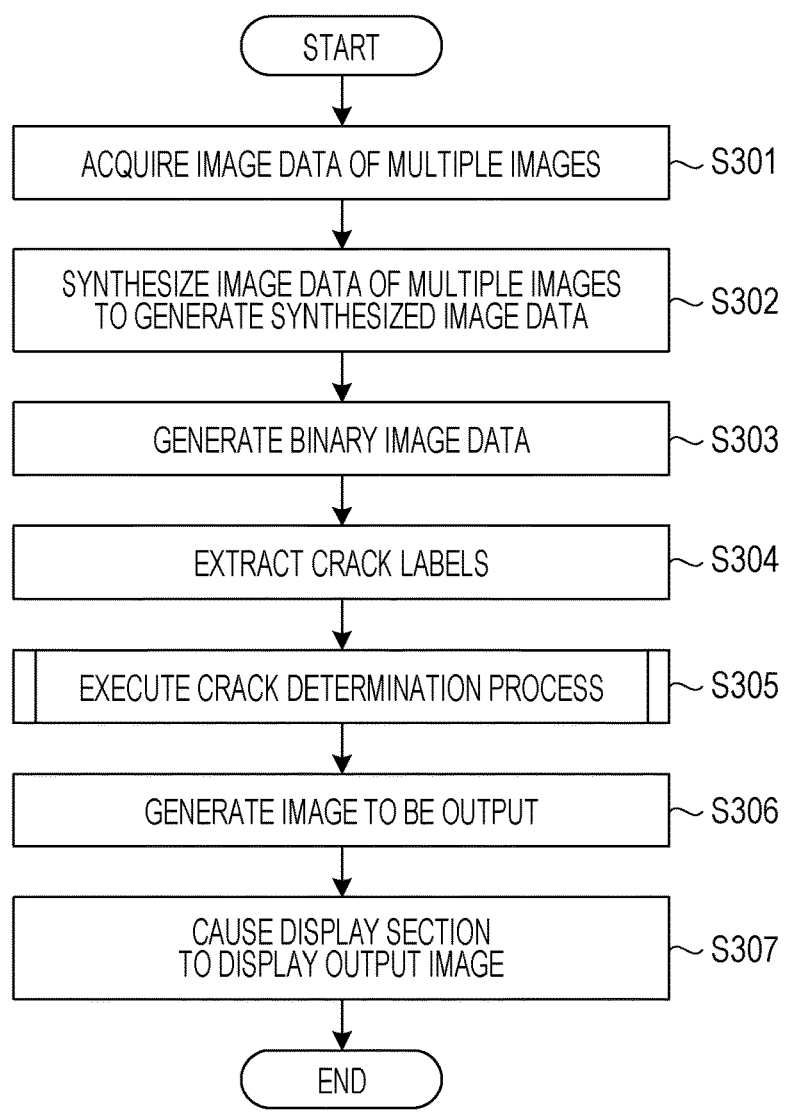
FIG. 11 is a flowchart of a process procedure of the image processing device according to the third embodiment.

Next, a process procedure of the image processing device 300 according to the third embodiment is described. FIG. 11 is a flowchart of the process procedure of the image processing device according to the third embodiment. As illustrated in FIG. 11, the acquiring section 161 of the image processing device 300 acquires image data of multiple images (in step S301). The synthesizing section 311 of the image processing device 300 synthesizes the image data of the multiple images to generate synthesized image data (in step S302).

The identifying section 162 of the image processing device 300 generates binary image data from the synthesized image data (in step S303). The identifying section 162 extracts crack labels (in step S304).

The evaluating section 165 of the image processing device 300 executes a crack determination process (in step S305). The crack determination process of step S305 corresponds to the processes of steps S104 to S109 illustrated in FIG. 6 in the first embodiment.

The output section 312 of the image processing device 300 generates an image to be output (in step S306). The output section 312 outputs the generated image to the display section 140 and causes the display section 140 to display the output image (in step S307).

Next, effects of the image processing device 300 according to the third embodiment are described. The image processing device 300 synthesizes image data stored in the image table 151 to generate synthesized image data of a single image indicating a whole target object and evaluates a crack based on the synthesized image data. Thus, even if a target object from which a crack may be detected is not included in image data of a single image, synthesized image data of the whole target object may be generated and the result of evaluating the crack may be notified.

Fourth Embodiment

Figure 12:
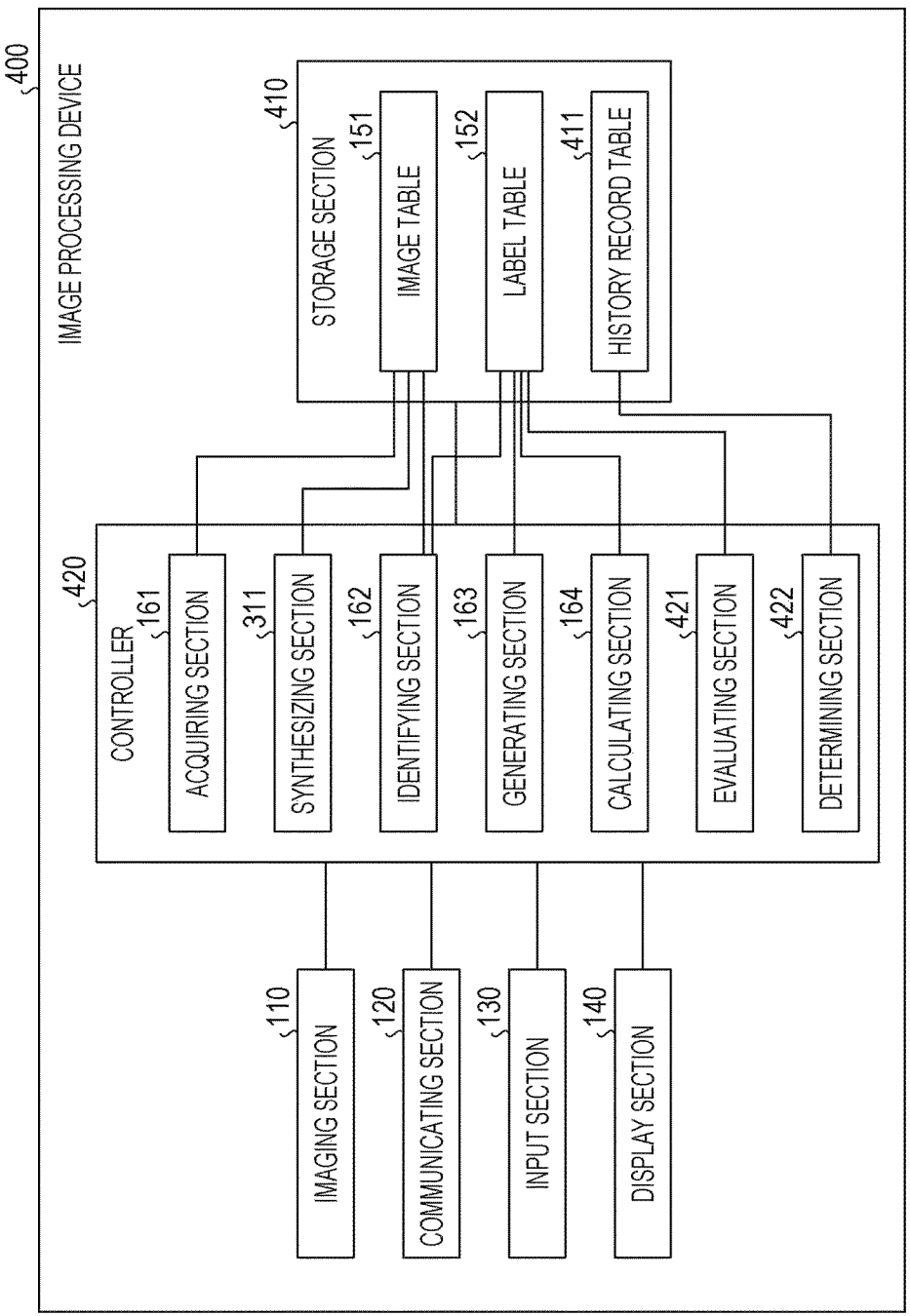
FIG. 12 is a block diagram illustrating a functional configuration of an image processing device according to a fourth embodiment.

FIG. 12 is a block diagram illustrating a functional configuration of an image processing device according to a fourth embodiment. The image processing device 400 includes an imaging section 110, a communicating section 120, an input section 130, a display section 140, a storage section 410, and a controller 420. A description of the imaging section 110, the communicating section 120, the input section 130, and the display section 140 is the same as or similar to the description of the imaging section 110, the communicating section 120, the input section 130, and the display section 140 with reference to FIG. 1.

It is assumed that an imaging range of the imaging section 110 is fixed. The imaging section 110 attaches information of dates and time when images are captured to image data and outputs the image data including the information to the controller 420.

The storage section 410 includes an image table 151, a label table 152, and a history record table 411. The storage section 410 corresponds to a semiconductor memory element such as a RAM, a ROM, or a flash memory or a storage device such as an HDD. A description of the image table 151 and the label table 152 is the same as or similar to the description of the image table 151 and the label table 152 with reference to FIG. 1.

The history record table 411 is a table that stores information of crack labels evaluated as cracks and information of imaging dates and time and in which the information of the crack labels is associated with the information of the imaging dates and time. FIG. 13 is a diagram illustrating an example of a data structure of the history record table. As illustrated in FIG. 13, in the history record table 411, imaging dates and time, label identification information, and region information items are associated with each other. The imaging dates and time indicate dates and time when image data is captured. The label identification information is information uniquely identifying crack labels evaluated as cracks. The region information items include positional coordinates of pixels included in the crack labels evaluated as the cracks. As illustrated, the same region information items may be registered as the region information items for different records of different label identification information, since a same crack will be imaged for several times at different dates and times, each associated with different label identification information.

The controller 420 includes an acquiring section 161, an identifying section 162, a generating section 163, a calculating section 164, a synthesizing section 311, an evaluating section 421, and a determining section 422. The controller 420 may be achieved by a CPU, an MPU, or the like. Alternatively, the controller 420 may be achieved by hard-wired logic such as an ASIC or an FPGA. A description of the acquiring section 161, the identifying section 162, the generating section 163, and the calculating section 164 is the same as or similar to the description of the acquiring section 161, the identifying section 162, the generating section 163, and the calculating section 164 with reference to FIG. 1. A description of the synthesizing section 311 is the same as or similar to the description of the synthesizing section 311 with reference to FIG. 10.

The evaluating section 421 is a processing section that evaluates crack labels of the label table 152 and identifies a crack label corresponding to a crack. A process of identifying the crack label corresponding to the crack by the evaluating section 421 is the same as or similar to the process to be executed by the evaluating section 165 described with reference to FIG. 1.

The evaluating section 421 associates label identification information and a region information item of a crack label corresponding to a crack with imaging date and time, and registers the label identification information, the region information item, and the imaging date and time in the history record table 411. The evaluating section 421 uses, as the information of the imaging date and time, information, attached to image data acquired from the imaging section 110, of date and time when an image is captured.

The determining section 422 is a processing section that determines, based on a past result of evaluating a crack and a present result of evaluating the crack, whether or not the area of a region of a crack label evaluated as the crack has increased. If the area of the region of the crack label has increased, the determining section 422 provides a notification indicating that the area of the region of the crack has increased. For example, the determining section 422 provides, to a terminal device of an administrator via a network, a warning indicating that the area of the crack has increased.

For example, the determining section 422 references the history record table 411, compares region information items associated with the latest imaging date and time with region information items associated with imaging date and time immediately before the latest imaging date and time, and identifies a pair of region information items indicating an overlapping region that is equal to or larger than a threshold. For example, imaging date and time of one of the region information items indicating the overlapping region that is equal to or larger than the threshold is different from imaging date and time of one of the region information items indicating the overlapping region that is equal to or larger than the threshold, but it may be said that cracks indicated by the pair of region information items are the same. If the determining section 422 compares an identified region information item associated with the latest imaging date and time with an identified region information item associated with the imaging date and time immediately before the latest imaging date and time, and a region indicated by the region information item associated with the latest imaging date and time is larger by the threshold or more than a region indicated by the region information item associated with the imaging date and time immediately before the latest imaging date and time, the determining section 422 determines that the area of a region of a crack has increased.

Figure 14:
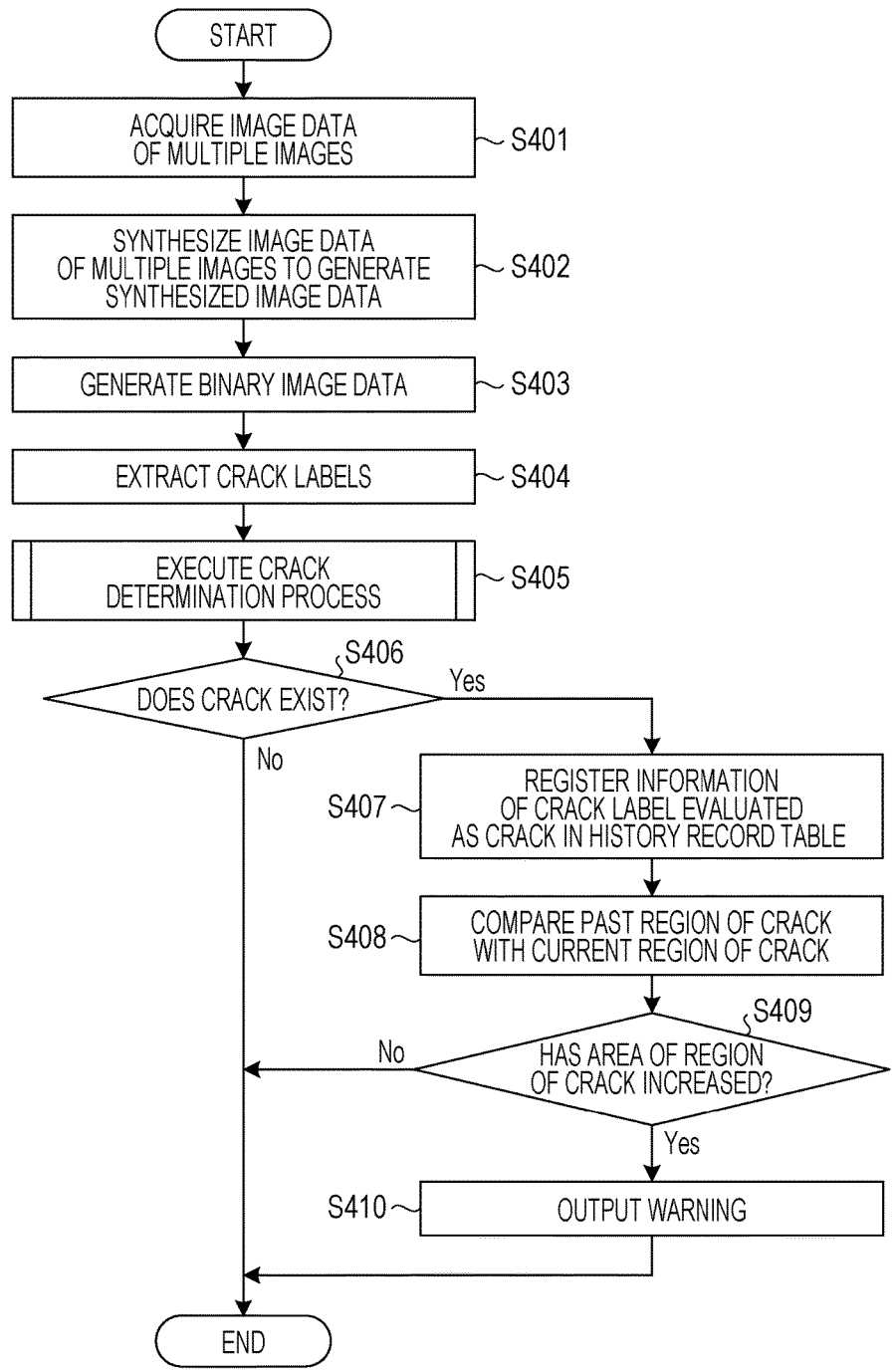
FIG. 14 is a flowchart of a process procedure of the image processing device according to the fourth embodiment.

Next, a process procedure of the image processing device 400 according to the fourth embodiment is described. FIG. 14 is a flowchart of the process procedure of the image processing device according to the fourth embodiment. As illustrated in FIG. 14, the acquiring section 161 of the image processing device 400 acquires image data of multiple images (in step S401). The synthesizing section 311 of the image processing device 400 synthesizes the image data of the multiple images to generate synthesized image data (in step S402).

The identifying section 162 of the image processing device 400 generates binary image data from the synthesized image data (in step S403). The identifying section 162 extracts crack labels (in step S404).

The evaluating section 421 of the image processing device 400 executes a crack determination process (in step S405). The crack determination process of step S405 corresponds to the processes of steps S104 to S109 illustrated in FIG. 6 in the first embodiment.

The evaluating section 421 determines whether or not a crack exists (in step S406). If the crack does not exist (No in step S406), the evaluating section 421 terminates the process. On the other hand, if the crack exists (Yes in step S406), the evaluating section 421 causes the process to proceed to step S407.

The evaluating section 421 registers information of a crack label evaluated as the crack in the history record table 411 (in step S407). The determining section 422 of the image processing device 400 compares a past region of the crack with a current region of the crack (in step S408). If the area of the region of the crack has not increased (No in step S409), the determining section 422 terminates the process.

On the other hand, if the area of the region of the crack has increased (Yes in step S409), the determining section 422 outputs a warning (in step S410).

Next, effects of the image processing device 400 according to the fourth embodiment are described. The image processing device 400 compares a past result of evaluating a crack with a current result of evaluating the crack. If the area of the region of the crack has increased, the image processing device 400 provides a notification indicating that the area of the region of the crack has increased. Thus, the administrator or the like may easily recognize that the area of the crack has increased.

Figure 15:
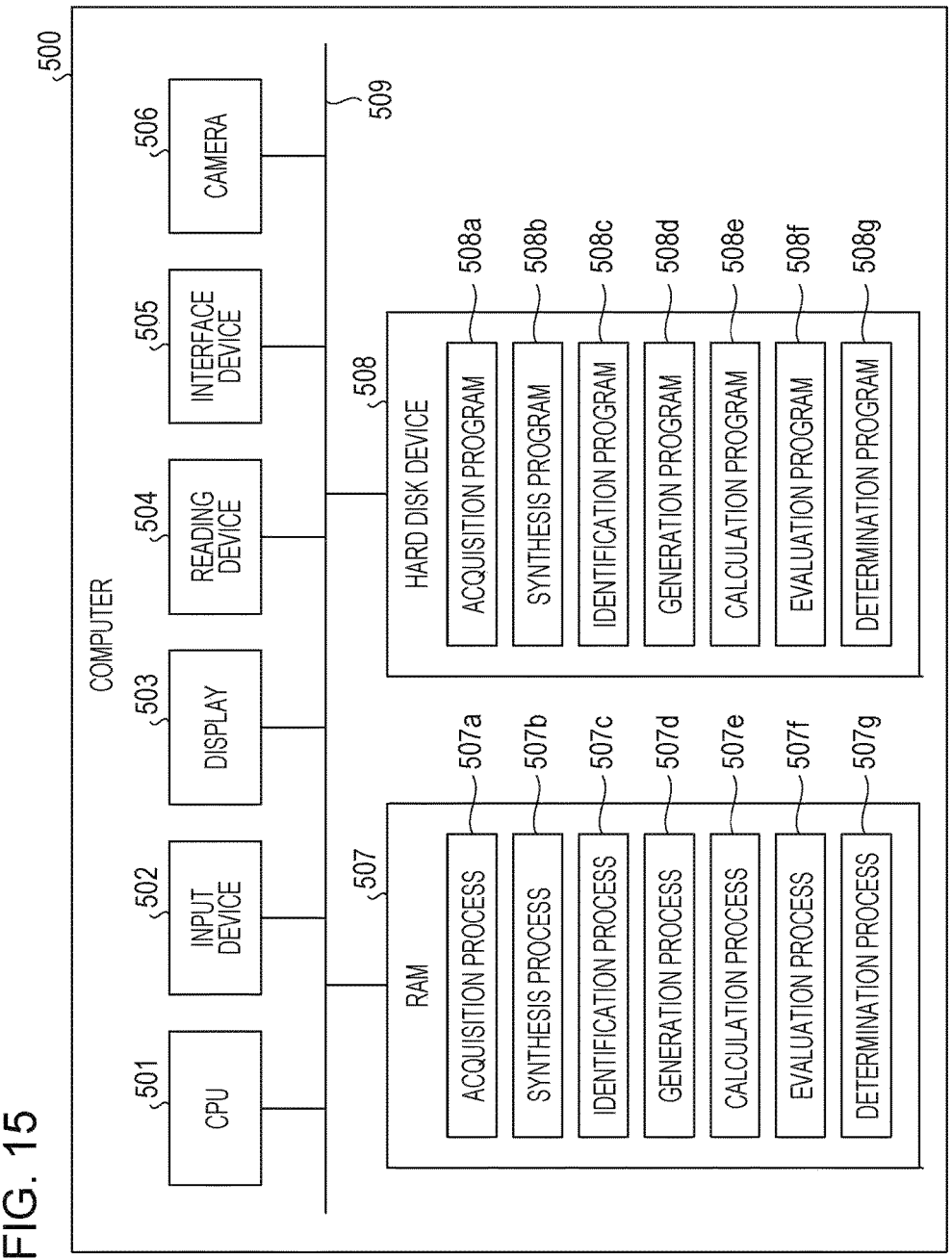
FIG. 15 is a diagram illustrating an example of a hardware configuration of a computer that achieves the same functions as the image processing devices.

Next, an example of a hardware configuration of a computer that achieves the same functions as those of the image processing devices 100, 200, 300, and 400 described in the embodiments is described. FIG. 15 is a diagram illustrating the example of the hardware configuration of the computer that achieves the same functions as those of the image processing devices.

As illustrated in FIG. 15, a computer 500 includes a CPU 501 for executing various types of arithmetic processing, an input device 502 for receiving the input of data from a user, and a display 503. The computer 500 further includes a reading device 504 for reading a program and the like from a storage medium and an interface device 505 for transmitting and receiving data to and from another computer via a network. The computer 500 further includes a camera 506. In addition, the computer 500 includes a RAM 507 for temporarily storing various types of information and a hard disk device 508. The devices 501 to 508 are connected to a bus 509.

The hard disk device 508 includes an acquisition program 508a, a synthesis program 508b, an identification program 508c, a generation program 508d, a calculation program 508e, an evaluation program 508f, and a determination program 508g. The CPU 501 reads the acquisition program 508a, the synthesis program 508b, the identification program 508c, the generation program 508d, the calculation program 508e, the evaluation program 508f, and the determination program 508g and loads the acquisition program 508a, the synthesis program 508b, the identification program 508c, the generation program 508d, the calculation program 508e, the evaluation program 508f, and the determination program 508g into the RAM 507.

The acquisition program 508a functions as an acquisition process 507a. The synthesis program 508b functions as a synthesis process 507b. The identification program 508c functions as an identification process 507c. The generation program 508d functions as a generation process 507d. The calculation program 508e functions as a calculation process 507e. The evaluation program 508f functions as an evaluation process 507f. The determination program 508g functions as a determination process 507g.

The acquisition process 507a corresponds to the processes to be executed by the acquiring section 161. The synthesis process 507b corresponds to the processes to be executed by the synthesizing section 311. The identification process 507c corresponds to the processes to be executed by the identifying section 162. The generation process 507d corresponds to the processes to be executed by the generating section 163. The calculation process 507e corresponds to the processes to be executed by the calculating section 164. The evaluation process 507f corresponds to the processes to be executed by the evaluating sections 165, 211, and 421. The determination process 507g corresponds to the processes to be executed by the determining section 422.

The programs 508a to 508g may not be stored in the hard disk device 508 in advance. For example, the programs 508a to 508g may be stored in a "portable physical medium" that is a flexible disk (FD), a CD-ROM, a DVD, a magneto-optical disc, an IC card, or the like and is to be inserted in the computer 500. The computer 500 may read the programs 508a to 508g from the portable physical medium and execute the programs 508a to 508g.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A computer-readable non-transitory storage medium storing an image processing program causing a computer to execute a process, the process comprising:
    identifying a dark region by binarizing an image captured using an imaging device;
    generating a line image corresponding to the dark region by thinning the identified dark region;
    identifying a first plurality of pairs of pixels that are included in a pixel group forming the generated line image and are separated from each other by a predetermined threshold or more;
    calculating a first variance of gradients of lines connecting the pixels forming the respective pairs in the first plurality of pairs of pixels;
    identifying a second plurality of pairs of pixels that are included in the pixel group forming the generated line image and are separated from each other by values smaller than the predetermined threshold;
    calculating a second variance of gradients of lines connecting the pixels forming the respective pairs in the second plurality of pairs of pixels; and
    evaluating the dark region based on the first variance and the second variance.

2. The storage medium according to claim 1,
    wherein the evaluating is to evaluate the dark region as a crack if the first variance is smaller than a first standard variance and the second variance is larger than a second standard variance.

3. The storage medium according to claim 2, the process further comprising:
    adjusting the standard variances based on the width of the dark region.

4. The storage medium according to claim 1, the process further comprising:
    combining, when a first dark region and a second dark region are identified in the identifying of the dark region, the first dark region with the second dark region by extending the first dark region and the second dark region to an intersection of the extended first dark region and the extended second dark region,
    wherein a first pixel from pixels belonging to a first line image generated by thinning the first dark region and a second pixel from pixels belonging to a second line image generated by thinning the second dark region are identified, where a distance between the first pixel and the second pixel is shortest among distances between the pixels belonging to the first line image and the pixels belonging to the second line image, and the intersection is determined as a cross point of a straight line extending from the first pixel in a direction in which the first line image extends and a straight line extending from the second pixel in a direction in which the second line image extends.

5. The storage medium according to claim 4,
    wherein if the distance between the first pixel and the second pixel is smaller than a predetermined distance, the combining is to combine the first dark region and the second dark region into a single dark region.

6. The storage medium according to claim 1, the process further comprising:
synthesizing a plurality of images captured using the imaging device to generate a synthesized image,
wherein the identifying of a dark region is to identify the dark region from the synthesized image.

7. The storage medium according to claim 2, the process further comprising:
outputting, based on the result of evaluating the dark region, an image indicating the position of the dark region evaluated as the crack.

8. The storage medium according to claim 1,
wherein the imaging device is installed in an unmanned aircraft.

9. The storage medium according to claim 2, the process further comprising:
determining, based on a past result of evaluating the dark region and a current result of evaluating the dark region, whether or not the area of the dark region evaluated as the crack has increased, and outputting the result of the determination.

10. An image processing method to be executed by a computer, comprising:
identifying a dark region by binarizing an image captured using an imaging device;
generating a line image corresponding to the dark region by thinning the identified dark region;
identifying a first plurality of pairs of pixels that are included in a pixel group forming the generated line image and are separated from each other by a predetermined threshold or more;
calculating a first variance of gradients of lines connecting the pixels forming the respective pairs in the first plurality of pairs of pixels;
identifying a second plurality of pairs of pixels that are included in the pixel group forming the generated line image and are separated from each other by values smaller than the predetermined threshold;
calculating a second variance of gradients of lines connecting the pixels forming the respective pairs in the second plurality of pairs of pixels; and
evaluating the dark region based on the first variance and the second variance.

11. An image processing device comprising:
a memory, and
a processor coupled to the memory and configured to execute a process, the process including;
identifying a dark region by binarizing an image captured using an imaging device;
generating a line image corresponding to the dark region by thinning the identified dark region;
identifying a first plurality of pairs of pixels that are included in a pixel group forming the generated line image and are separated from each other by a predetermined threshold or more;
calculating a first variance of gradients of lines connecting the pixels forming the respective pairs in the first plurality of pairs of pixels;
identifying a second plurality of pairs of pixels that are included in the pixel group forming the generated line image and are separated from each other by values smaller than the predetermined threshold;
calculating a second variance of gradients of lines connecting the pixels forming the respective pairs in the second plurality of pairs of pixels; and
evaluating the dark region based on the first variance and the second variance.

* * * * *